US010702700B2

(12) United States Patent
Shah et al.

(10) Patent No.: US 10,702,700 B2
(45) Date of Patent: Jul. 7, 2020

(54) HYBRID IMPLANTABLE CONNECTORS

(71) Applicant: Verily Life Sciences LLC, South San Francisco, CA (US)

(72) Inventors: Kedar Shah, San Francisco, CA (US); Shivkumar Sabesan, San Mateo, CA (US); Brian Pepin, San Francisco, CA (US); Jared Floyd, Ferndale, WA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 200 days.

(21) Appl. No.: 15/995,933

(22) Filed: Jun. 1, 2018

(65) Prior Publication Data

US 2018/0345023 A1 Dec. 6, 2018

Related U.S. Application Data

(60) Provisional application No. 62/514,190, filed on Jun. 2, 2017.

(51) Int. Cl.
*A61N 1/372* (2006.01)
*A61B 5/00* (2006.01)
*A61N 1/05* (2006.01)
*A61N 1/375* (2006.01)
*A61N 1/37* (2006.01)

(52) U.S. Cl.
CPC ............ *A61N 1/372* (2013.01); *A61B 5/0031* (2013.01); *A61N 1/0551* (2013.01); *A61N 1/3752* (2013.01); *A61N 1/05* (2013.01); *A61N 1/37* (2013.01)

(58) Field of Classification Search
None
See application file for complete search history.

(56) References Cited

U.S. PATENT DOCUMENTS

| 8,500,355 | B2 | 8/2013 | Liu |
| 8,651,340 | B2 | 2/2014 | Lelieveld et al. |
| 8,738,149 | B2 | 5/2014 | Greenberg et al. |
| 9,211,377 | B2 | 12/2015 | Kruse et al. |
| 9,308,382 | B2 | 4/2016 | Pack et al. |
| 2004/0261790 | A1 | 12/2004 | Joshi et al. |
| 2008/0208283 | A1 | 8/2008 | Vetter et al. |
| 2009/0124994 | A1 | 5/2009 | Roe et al. |
| 2011/0072657 | A1 | 3/2011 | Swanson et al. |

(Continued)

OTHER PUBLICATIONS

International Application No. PCT/US2018/035639, "International Preliminary Report on Patentability", dated Dec. 12, 2019, 9 pages.

(Continued)

*Primary Examiner* — Brian T Gedeon
(74) *Attorney, Agent, or Firm* — Kilpatrick Townsend & Stockton LLP

(57) ABSTRACT

A hybrid connector for connecting a bulk conductor to a planar strand of a flexible circuit is described. The hybrid connector can include a connector body, a first connector end, and a second connector end. The first connector end can be attached to the connector body and can define a first opening having a first cross-sectional shape that corresponds to a first distal end of the strand. The second connector end can be attached to the connector body opposite the first connector end and can define a second opening having a second cross-sectional shape that corresponds to a second distal end of the bulk conductor.

35 Claims, 9 Drawing Sheets

(56) References Cited

U.S. PATENT DOCUMENTS

| | | |
|---|---|---|
| 2011/0238145 A1 | 9/2011 | Swanson |
| 2013/0338586 A1 | 12/2013 | Dickinson et al. |
| 2015/0094789 A1 | 4/2015 | Janzig et al. |
| 2015/0165216 A1 | 6/2015 | Hughes et al. |
| 2016/0193460 A1 | 7/2016 | Xu et al. |
| 2016/0346530 A1 | 12/2016 | Jeffery et al. |

OTHER PUBLICATIONS

PCT/US2018/035639 , "International Search Report and Written Opinion", dated Sep. 12, 2018, 13 pages.
Medtronic , Restoresensor Surescan MRI Neurostimulator (http://www.medtronic.com/us-en/patients/treatments-therapies/drug-pump-chronic-pain/neurostimulators-restore-sensor.html), Copyright 2017.
Second Sight , (http://www.secondsight.com/system-overview-en.html), Copyright 2016.

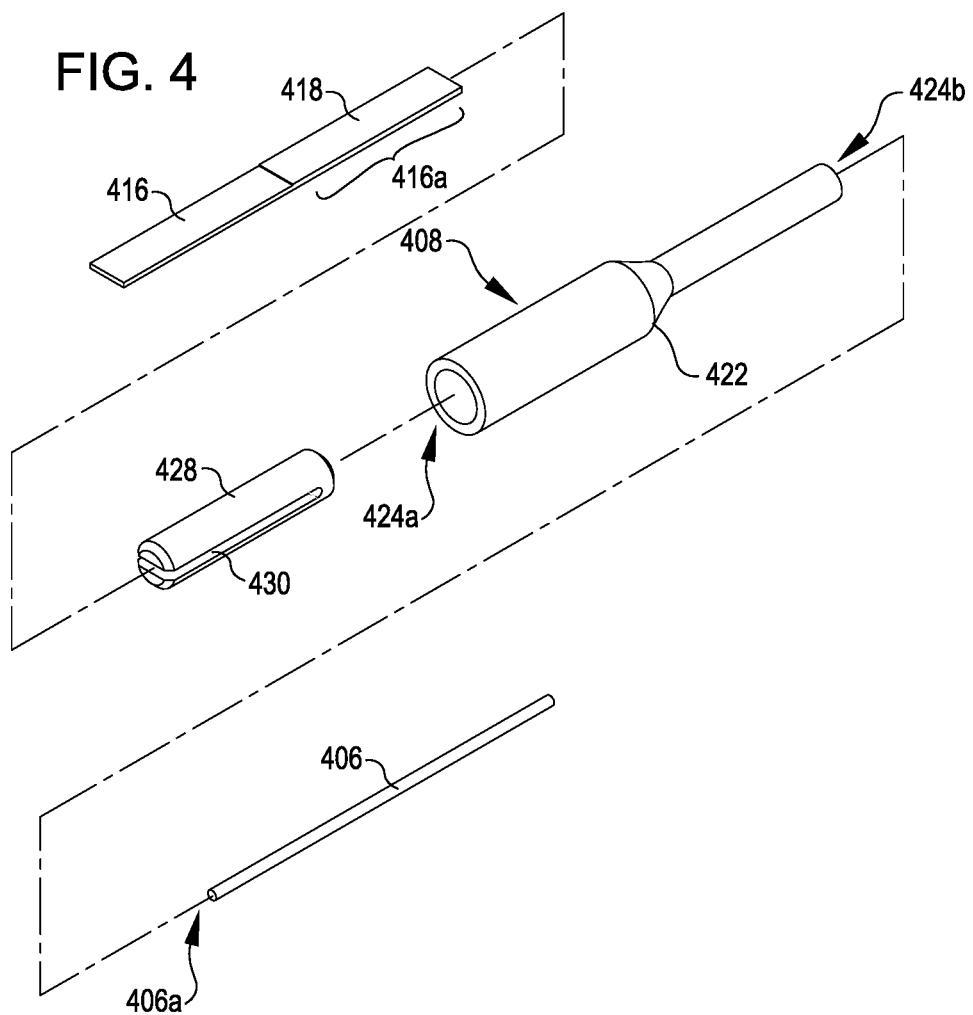
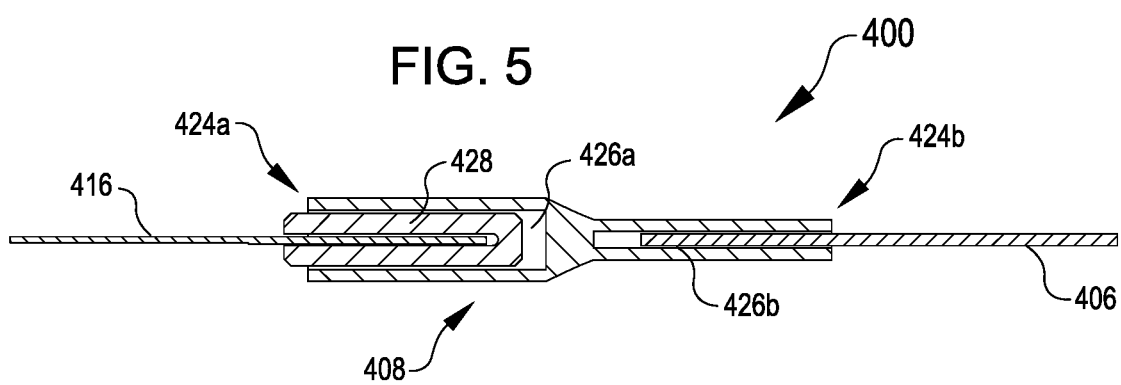

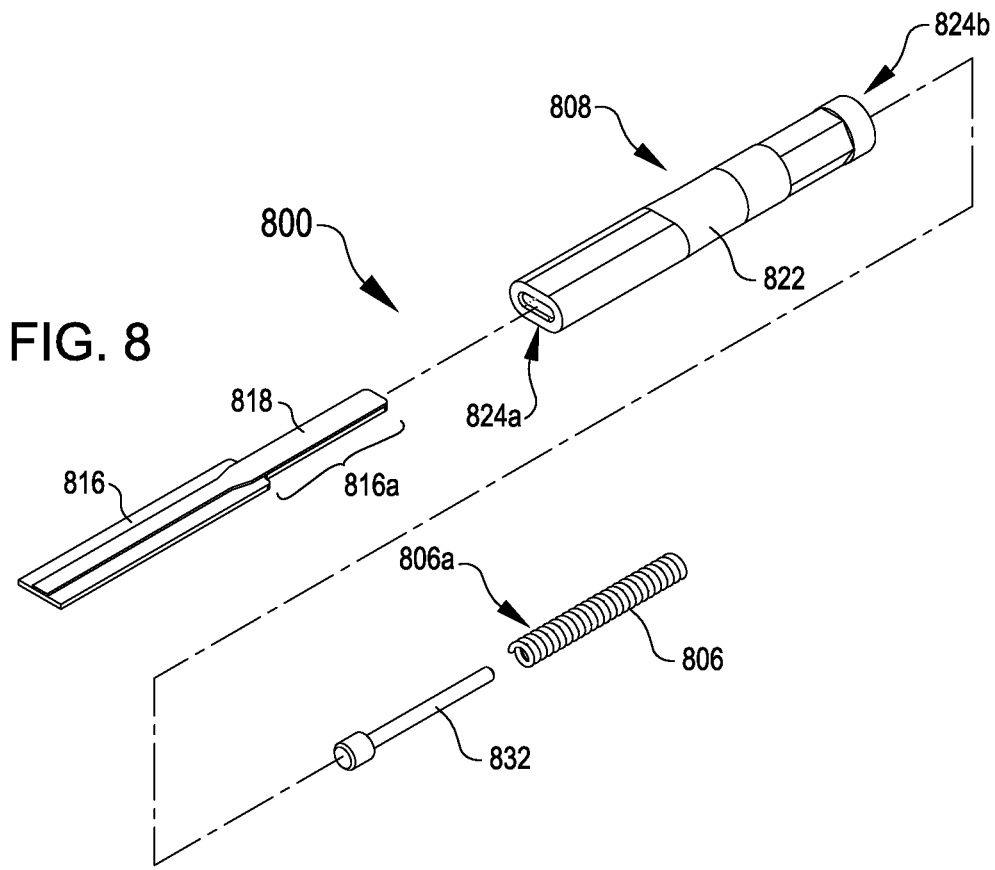

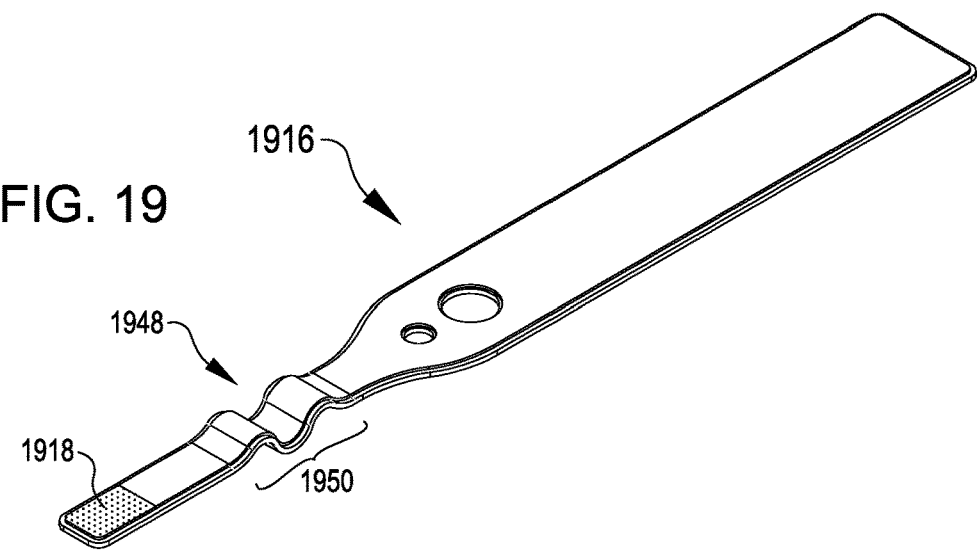

FIG. 19

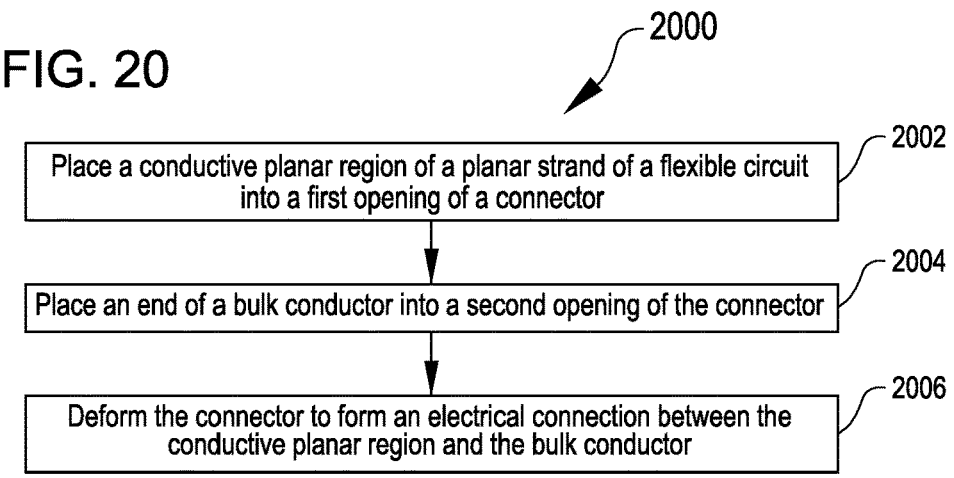

FIG. 20

- 2002 Place a conductive planar region of a planar strand of a flexible circuit into a first opening of a connector
- 2004 Place an end of a bulk conductor into a second opening of the connector
- 2006 Deform the connector to form an electrical connection between the conductive planar region and the bulk conductor

FIG. 21

- 2102 Align a set of openings formed in a conductive planar region of a planar strand of a flexible circuit with a set of tabs of a connector
- 2104 Place an end of a bulk conductor into an opening of the connector
- 2106 Deform the connector to form an electrical connection between the conductive planar region and the bulk conductor

HYBRID IMPLANTABLE CONNECTORS

CROSS-REFERENCE TO RELATED APPLICATIONS

The present application claims priority to Provisional Application No. 62/514,190, filed on Jun. 2, 2017, and entitled "Hybrid Implantable Connectors," the entirety of which is hereby incorporated by reference herein.

BACKGROUND

Implantable medical devices can be used for monitoring (e.g., ongoing glucose monitoring) and for stimulation (e.g., to regulate the beating of a heart). An example device can include an electronics package connected to one or more leads via a connector. The one or more leads can be placed at a target location for monitoring or stimulation. In a monitoring scenario, the leads gather information from the target location and the electronics package processes the information. In a stimulation scenario, the electronics package generates electrical signals that are delivered to the target location via the leads.

SUMMARY

Various examples are described relating to hybrid connectors, connection systems including hybrid connectors, and methods for forming connections using hybrid connectors.

In an example, a system is described. The system includes a connector defining a cavity and a flexible circuit. A first opening is formed at a first end of the connector and a second opening is formed at a second end of the connector. The first opening defines a first connector cross-sectional shape. The flexible circuit defines a neural interface and includes an elongate planar strand. The elongate planar strand includes a conductive region disposed at a distal end of the elongate planar strand. The distal end includes a strand cross-sectional shape. A portion of the conductive region of the elongate planar strand is disposed within the first opening.

In another example, a hybrid connector is described. The hybrid connector includes a connector body, a first connector end attached to the connector body, and a second connector end attached to the connector body opposite the first connector end. The first connector defines a first opening defining a first cross-sectional shape that corresponds to a first distal end of a planar flexible circuit. The second connector end defines a second opening defining a second cross-sectional shape that corresponds to a second distal end of a bulk conductor.

In yet another example, a hybrid connector is described. The hybrid connector includes a connector body, a first connector end attached to the connector body, and a second connector end attached to the connector body opposite the first connector end. The first connector end includes a set of raised tabs corresponding to a set of openings formed in a distal region of a planar flexible circuit. The second connector end defines an opening defining a cross-sectional shape that corresponds to a distal end of a bulk conductor.

In yet another example, a system is described. The system includes a neural interface comprising an elongate planar strand. The elongate planar strand includes a conductive region disposed at a first distal end of the elongate planar strand. The first distal end includes a first cross-sectional shape. The system also includes a bulk conductor including a second distal end that includes a second cross-sectional shape. The system also includes a connector disposed between the elongate planar strand and the bulk conductor. The connector includes a first end in which is formed a first opening corresponding to the first cross-sectional shape. The first distal end is held within the first opening. The connector also includes a second end in which is formed a second opening corresponding to the second cross-sectional shape. The second distal end is held within the second opening. An electrical connection is formed between the conductive region and the bulk conductor via the connector.

In yet another example, a method is described. The method includes placing a conductive planar region of a planar strand of a flexible circuit into a first opening of a connector. The method also includes placing an end of a bulk conductor into a second opening of the connector. The method also includes deforming the connector to form an electrical connection between the conductive planar region and the bulk conductor.

In yet another example, a method is described. The method includes aligning a set of openings formed in a conductive planar region of a planar strand of a flexible circuit with a set of tabs of a connector. The set of tabs is disposed at a first end of the connector. The method includes placing an end of a bulk conductor into an opening of the connector. The opening is disposed at a second end of the connector. The method also includes deforming the connector to form an electrical connection between the conductive planar region and the bulk conductor.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIG. 4 illustrates an exploded view of an example connection system including a hybrid connector, according to at least one example.

FIG. 5 illustrates a profile view of the connection system of FIG. 4, according to at least one example.

FIG. 8 illustrates an exploded view of an example connection system including a hybrid connector, according to at least one example.

FIG. 9 illustrates a profile view of the connection system of FIG. 8, according to at least one example.

FIG. 19 illustrates a perspective view of an example flexible circuit including a series of curves, according to at least one example.

FIG. 20 illustrates an example flow diagram illustrating a process of forming a connection system, according to at least one example.

FIG. 21 illustrates an example flow diagram illustrating a process of forming a connection system, according to at least one example.

DETAILED DESCRIPTION

Figure 1:
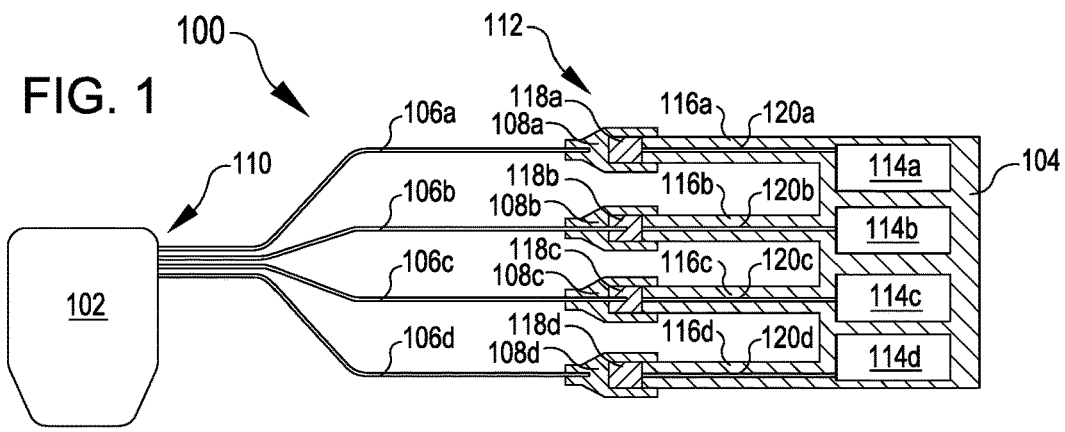
FIG. 1 illustrates a top view of a neurostimulation system including example connection systems, according to at least one example.

Examples are described herein in the context of connection systems including hybrid connectors for use in neurostimulation devices and/or monitoring devices. Those of ordinary skill in the art will realize that the following description is illustrative only and is not intended to be in any way limiting. For example, the connection systems described herein can also be used for other applications in which connections are made between flexible circuits and bulk conductors. In some examples, the connection systems can be used in applications that are not implanted in human tissue. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example, hybrid connectors are used to connect electrical traces of a neural interface with bulk conductors (e.g., leads). The bulk conductors transport electrical signals between the neural interface and an electronics package. The neural interface is microfabricated as a flexible circuit with a set of elongate planar strands extending away from a main body of the neural interface. Each elongate planar strand includes a bond pad, and the number of elongate planar strands corresponds to the number of bulk conductors. To form a connection, a single bulk conductor is aligned with a single strand of the flexible circuit. A hybrid connector formed as a metal sleeve is provided between the single bulk conductor and the single strand of the flexible circuit. The hybrid connector is adapted to receive the bulk conductor, which may have a circular cross section, and the strand of the flexible circuit, which may have a rectangular cross section. An end of the single bulk conductor and an end of the single strand of the flexible circuit are inserted into opposing ends of the hybrid connector. An electrical connection is made between the hybrid connector and the bulk conductor and the strand by deforming the hybrid connector (e.g., mechanically crimping). The remaining bulk conductors can be independently connected to the remaining elongate planar strands in a similar manner using independent hybrid connectors.

This illustrative example is given to introduce the reader to the general subject matter discussed herein and the disclosure is not limited to this example. The following sections describe various additional non-limiting examples of connection systems using hybrid connectors.

Referring now to FIG. 1, FIG. 1 illustrates a neurostimulation system 100, according to at least one example. The neurostimulation system 100 includes a neurostimulation device 102, a neural interface 104, and a set of bulk conductors (e.g., electrode leads) 106 extending between the neurostimulation device 102 and the neural interface 104. As described in detail herein, the set of bulk conductors 106 is electrically connected to the neural interface 104 via a set of hybrid connectors 108.

The neurostimulation device 102 can be any suitable active implantable device such as those for neuromodulation or neurostimulation. Examples of such devices include deep brain stimulators, cochlear implants, cardiac pacemakers, bioelectric devices, peripheral nerve stimulation systems, and other similar devices. In some examples, a monitoring device is used in place of the neurostimulation device 102. In this example, the monitoring device can be attached to the neural interface 104 in order to monitor conditions of a patient's health. Examples of such devices include those used for glucose monitoring. Such devices may also include those used for glucose monitoring and delivery.

In some examples, all or a portion of the set of bulk conductors 106 is carried within a flexible cable between the neurostimulation device 102 and the neural interface 104. First distal ends 110 of the bulk conductors 106 (e.g., those located adjacent to the neurostimulation device 102) can be formed into a plug (e.g., a planar array of contacts, a cylindrical array of contacts, or other similar contact distribution). The plug can interface with a corresponding socket of the neurostimulation device 102 to detachably couple the bulk conductors 106 with the neurostimulation device 102. Second distal ends 112 of the bulk conductors 106 (e.g., those located adjacent to the hybrid connectors 108) are connected to the neural interface 104 via the hybrid connectors 108.

The bulk conductors 106 can take any suitable form factor and can be formed from any suitable bio compatible conductive material such as gold, titanium, platinum, iridium, niobium, platinum alloy, iridium alloy, nickel titanium alloy, nickel-cobalt-chromium-molybdenum alloy (e.g., MP35N®), or any other suitable material. The bulk conductors 106 can be coated with a flexible, insulative material such as silicon, polyurethane, Teflon®, or some other similar material.

The neural interface 104 is formed as a flexible circuit (e.g., flex circuit, flexible printed circuit board, flex print, flex-circuit, and other similar flexible circuit). In some examples, the neural interface 104 is formed using a microfabrication technique. Thus, the neural interface 104 can be a flexible microfabricated circuit board. The neural interface 104 can be formed from polyimide, paraben, liquid crystal polymer, polyether ether ketone (PEEK), plain polyester film (PEP), or any other similar material.

The neural interface 104 includes an array of electrodes 114. Each of the electrodes 114 can be placed at one or many target locations within the tissue, depending on the implementation. While the array of electrodes 114 is shown as an electrode cuff, it is understood that the electrodes 114 may take other form factors, including, for example, independent electrodes that can be spaced and placed separate from each other. The dimensions of the electrodes 114 can vary depending on the application.

The neural interface 104 also includes a set of flexible strands 116. The flexible strands 116 can be formed from the same material and as part of the process as the other portions of the neural interface 104. In some examples, the neural interface 104 is formed as a single sheet including multiple layers of insulative and conductive material. The flexible strands 116 can be cut from this sheet to have the elongate form as shown in FIG. 1.

Each flexible strand 116 includes a bond pad 118 which is electrically connected to one of the electrodes 114 via an electrical trace 120 of the neural interface 104. The bond pads 118 are conductive regions on the flexible strands 116 wherein electrical connections can be made with the bulk conductors 106. The bond pads 118 can be located adjacent to distal ends of the flexible strands 116. The bond pads 118 can be formed from any suitable bio compatible conductive material such as gold, titanium, platinum, iridium, niobium, platinum alloy, iridium alloy, nickel titanium alloy, nickel-cobalt-chromium-molybdenum alloy (e.g., MP35N®), or any other suitable material.

The flexible strands 116 may have a generally rectangular cross section and take the form of a thin flexible ribbon. The bulk conductors 106 may have a generally circular cross section and may take the form of a semi-stiff wire. The hybrid connectors 108 are configured to enable connection of these two different structures having vastly different geometries.

Depending on the implementation, different varieties of hybrid connectors 108 can be utilized. For example, some hybrid connectors 108 such as hybrid connectors 108*a* and 108*d* may hold the bulk conductors 106*a* and 106*d* and the bond pads 118*a* and 118*d* in an end-to-end orientation (e.g., second distal ends 112 of the bulk conductors 106 can be aligned with the bond pads 118 without actually physically contacting the bond pads 118). The hybrid connectors 108*b* and 108*c* may hold the bulk conductors 106*b* and 106*c* and the bond pads 118*b* and 118*c* in an overlapping orientation (e.g., the bulk conductors 106 can physically contact and overlap the bond pads 118).

The hybrid connectors 108 can take any suitable form factor as described herein and can be formed from any suitable bio compatible conductive material such as gold, titanium, platinum, iridium, niobium, platinum alloy, iridium alloy, nickel titanium alloy, nickel-cobalt-chromium-molybdenum alloy (e.g., MP35N®), or any other suitable material.

In some examples, the neural interface 104 along with the bulk conductors 106 and the hybrid connectors 108 are implanted in a person's body through one or more incisions. As part of the same surgery, the neurostimulation device 102 can also be installed in the person's body.

Figure 2:
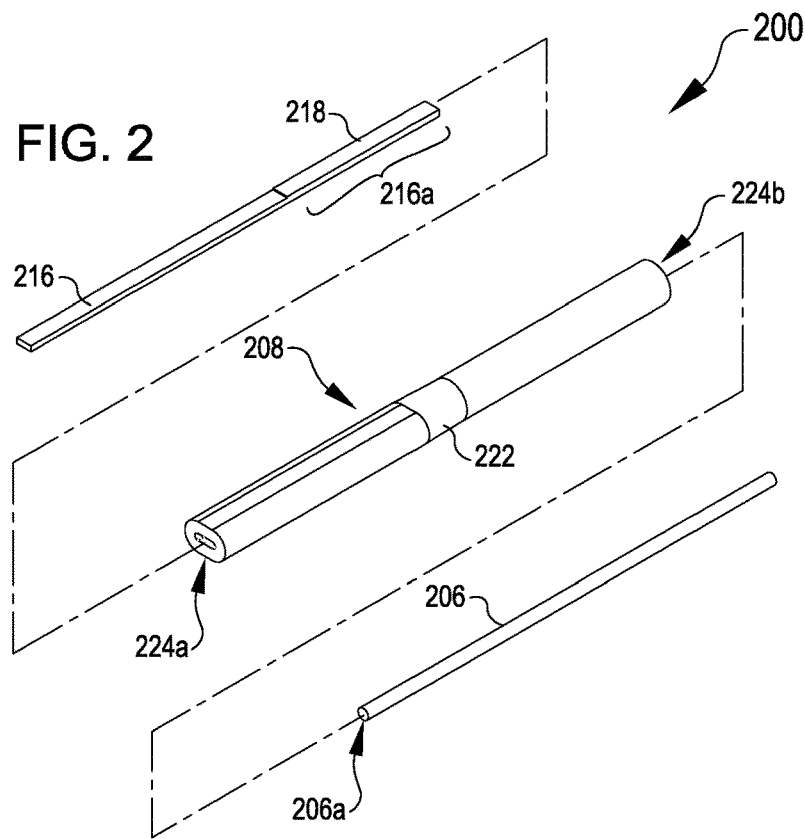
FIG. 2 illustrates an exploded view of an example connection system including a hybrid connector, according to at least one example.
Figure 3:
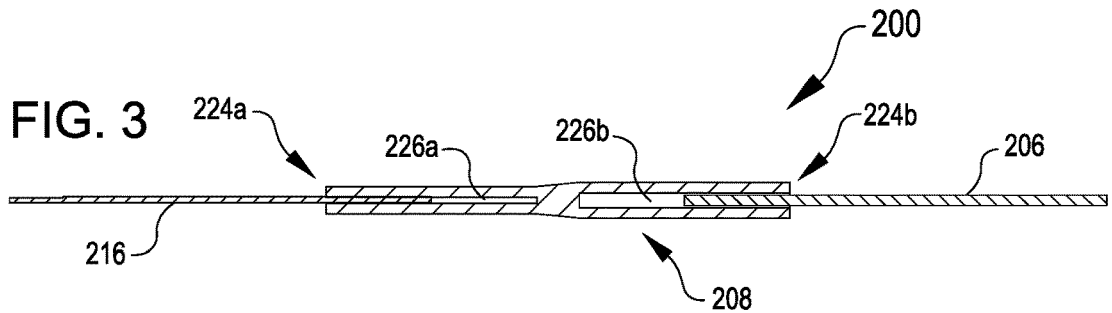
FIG. 3 illustrates a profile view of the connection system of FIG. 2, according to at least one example.

FIGS. 2 and 3 respectively illustrate an exploded view of an example connection system 200 including a hybrid connector 208 and a profile view of the connection system 200, according to at least one example. In addition to the hybrid connector 208, the connection system 200 includes a bulk conductor 206 and a flexible strand 216.

The bulk conductor 206 can take any suitable form factor such as those described herein. Likewise the flexible strand 216 can take any suitable form factor such as those described herein. In some examples, a bond pad 218 is formed in a distal region 216*a* of the flexible strand 216.

The hybrid connector 208 is formed as a sleeve defined by a body portion 222 and two ends 224*a*, 224*b*. The body portion 222 includes an opening 226*a* adjacent to the end 224*a* and an opening 226*b* adjacent to the end 224*b*. In some examples, the openings 226*a*, 226*b* are connected to each to each to define a continuous cavity within the body portion 222. The interior of the hybrid connector 208 can include anchors to engage with objects inserted into the openings 226.

The hybrid connector 208 and any other portion of the connection system 200 can be coated with an epoxy or other similar material. Such material may add extensibility to the connection system 200.

A cross-sectional shape of the opening 226*a* taken at the end 224*a* corresponds to a cross-sectional shape of the flexible strand 216. For example, the flexible strand 216 can have a rectangular cross-sectional shape and the opening 226*a* can have a similar shape, but be sized slightly larger in order to receive the flexible strand 216 (e.g., a portion of the distal region 216*a* that includes the bond pad 218).

A cross-sectional shape of the opening 226*b* taken at the end 224*b* corresponds to a cross-sectional shape of the bulk conductor 206. For example, the bulk conductor 206 can have a circular cross-sectional shape and the opening 226*b* can have similar shape, but can be sized slightly larger in order to receive a distal portion of the bulk conductor 206.

An electrical and mechanical connection is formed between the bulk conductor 206 and the bond pad 218 via the hybrid connector 208. This can be achieved by bonding the bulk conductor 206 and the bond pad 218 to the hybrid connector 208 using any suitable technique or combination of techniques. Such bonding can be achieved using a crimping technique, a thermocompression bonding technique, a thermosonic bonding technique, a resistance welding technique, a laser welding technique, conductive epoxy, and/or any other bonding technique suitable for bonding the bulk conductor 206 and/or the bond pad 218 to the hybrid connector 208.

For example, the hybrid connector 208 can be mechanically crimped to the bulk conductor 206 and the bond pad 218. In some examples, a first crimping tool can be used to crimp the body portion 222 that includes the opening 226*a* and a second crimping tool can be used to crimp the body portion 222 that includes the opening 226*b*. In some examples, a single crimping tool is used to crimp both portions of the body 222. The crimping process may also include the addition of elevated temperature, welding, and/or ultrasonic energy in order to mechanically and electrically couple the hybrid connector 208 to the bulk conductor 206 and the bond pad 218. As part of the same process or a different process, the openings 226*a*, 226*b* can be filled with a conductive epoxy to electrically connect, or further electrically connect, the bulk conductor 206 and the bond pad 218 to the hybrid connector 208.

FIGS. 4 and 5 respectively illustrate an exploded view of an example connection system 400 including a hybrid connector 408 and a profile view of the connection system 400, according to at least one example. In addition to the hybrid connector 408, the connection system 400 includes a bulk conductor 406 and a flexible strand 416.

The bulk conductor 406 can take any suitable form factor such as those described herein. Likewise the flexible strand 416 can take any suitable form factor such as those described herein. In some examples, a bond pad 418 is formed in a distal region 416a of the flexible strand 416.

The hybrid connector 408 is formed as a sleeve defined by a body portion 422 and two ends 424a, 424b. The body portion 422 includes an opening 426a adjacent to the end 424a and an opening 426b adjacent to the end 424b. In some examples, the openings 426a, 426b are connected to each to each to define a continuous cavity within the body portion 422.

A cross-sectional shape of the opening 426a taken at the end 424a corresponds to a cross-sectional shape of a slug 428 to be inserted into the opening 426a. For example, the slug 428 and the opening 426a can have circular cross-sectional shapes. In some examples, the cross-sectional shapes are non-circular and uniform (e.g., square, rectangular, triangular, oval, etc.).

In some examples, the slug is formed from an electrically conductive material and is used to equally distribute crimping forces on the bond pad 418.

The slug 428 also includes a slot 430. The slot 430 is sized to receive the flexible strand 416. In particular, the distal region 416a of the flexible strand 416 can be inserted into the slot 430 and the slug 428 can be inserted into the opening 426a. Thus, the slot 430 can have a cross-sectional shape that corresponds to the cross-sectional shape of the flexible strand 416. In this example, the flexible strand 416 can have a rectangular cross-sectional shape and the slot 430 can have a similar shape, but be sized slightly larger in order to receive the flexible strand 416 therein (e.g., a portion of the distal region 416a that includes the bond pad 418).

A cross-sectional shape of the opening 426b taken at the end 424b corresponds to a cross-sectional shape of the bulk conductor 406. For example, the bulk conductor 406 can have a circular cross-sectional shape and the opening 426b can have similar shape, but can be sized slightly larger in order to receive a distal portion of the bulk conductor 406.

An electrical and mechanical connection is formed between the bulk conductor 406 and the bond pad 418 via the hybrid connector 408. This can be achieved by bonding the bulk conductor 406 and the bond pad 418 to the hybrid connector 408 using any suitable technique or combination of techniques. Such bonding can be achieved using a crimping technique, a thermocompression bonding technique, a thermosonic bonding technique, a resistance welding technique, a laser welding technique, conductive epoxy, and/or any other bonding technique suitable for bonding the bulk conductor 406 and/or the bond pad 418 to the hybrid connector 408.

For example, the hybrid connector 408 can be mechanically crimped to the bulk conductor 406 and the bond pad 418. In some examples, a first crimping tool can be used to crimp the body portion 422 that includes the opening 426a and a second crimping tool can be used to crimp the body portion 422 that includes the opening 426b. In some examples, a single crimping tool is used to crimp both portions of the body 422. The crimping process may also include the addition of elevated temperature and/or welding in order to mechanically and/or electrically couple the hybrid connector 408 to the bulk conductor 406 and the bond pad 418. As part of the same process or a different process, the openings 426a, 426b can be filled with a conductive epoxy to electrically connect, or further electrically connect, the bulk conductor 406 and the bond pad 418 to the hybrid connector 408.

Figure 6:
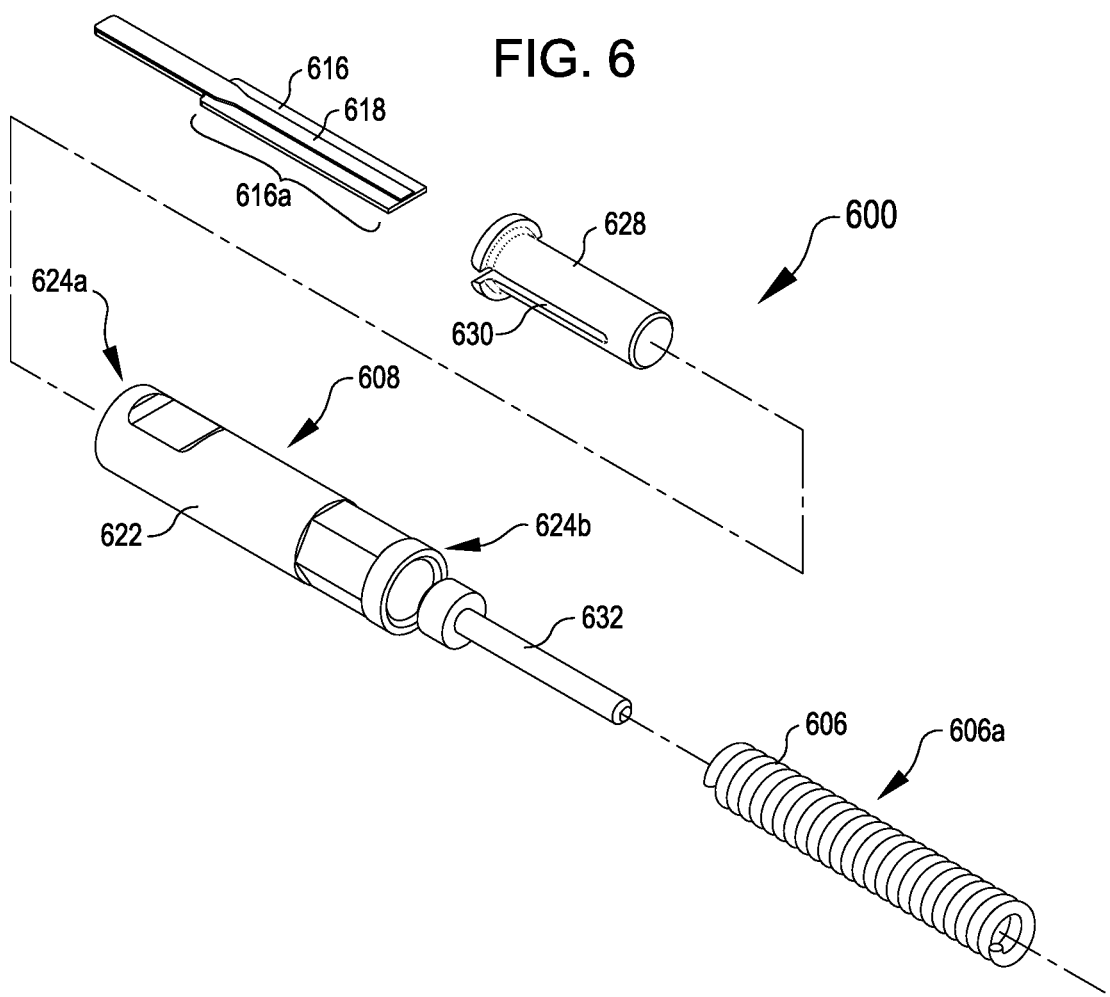
FIG. 6 illustrates an exploded view of an example connection system including a hybrid connector, according to at least one example.
Figure 7:
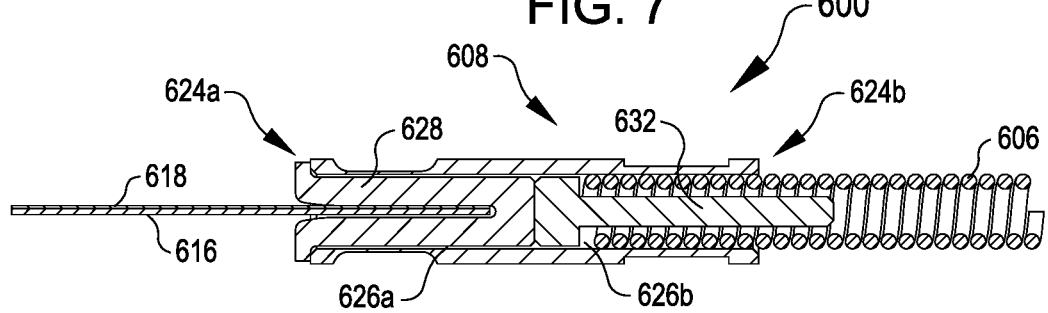
FIG. 7 illustrates a profile view of the connection system of FIG. 6, according to at least one example.

FIGS. 6 and 7 respectively illustrate an exploded view of an example connection system 600 including a hybrid connector 608 and a profile view of the connection system 600, according to at least one example. In addition to the hybrid connector 608, the connection system 600 includes a bulk conductor 606 and a flexible strand 616.

The bulk conductor 606 can take any suitable form factor such as those described herein. For example, the bulk conductor 606 has a coiled form factor. In some examples, the coiled form may provide extensibility in the connection system 600. The flexible strand 616 can take any suitable form factor such as those described herein. For example, the flexible strand 616 can be planar and elongate. In some examples, a bond pad 618 is formed in a distal region 616a of the flexible strand 616. In this example, the bond pad 618 extends along a middle top surface of the flexible strand 616. Any of the bond pads described herein can be disposed on one or more surfaces of the flexible strands. For example, a bond pad can extend along a top surface, a bottom surface, side surfaces, and/or an end surface of an example flexible strand.

The hybrid connector 608 is formed as a sleeve defined by a body portion 622 and two ends 624a, 624b. The body portion 622 includes an opening 626a adjacent to the end 624a and an opening 626b adjacent to the end 624b. In some examples, the openings 626a, 626b are connected to each to each to define a continuous cavity within the body portion 622.

A cross-sectional shape of the opening 626a taken at the end 624a corresponds to a cross-sectional shape of a slug 628 to be inserted into the opening 626a. For example, the slug 628 and the opening 626a can have circular cross-sectional shapes. In some examples, the cross-sectional shapes are non-circular and uniform (e.g., square, rectangular, triangular, oval, etc.).

In some examples, the slug 628 is formed from an electrically conductive material and is used to equally distribute crimping forces on the bond pad 618.

The slug 628 also includes a slot 630. The slot 630 is sized to receive the flexible strand 616. In particular, the distal region 616a of the flexible strand 616 can be inserted into the slot 630 and the slug 628 can be inserted into the opening 626a. Thus, the slot 630 can have a cross-sectional shape that corresponds to the cross-sectional shape of the flexible strand 616. In this example, the flexible strand 616 can have a rectangular cross-sectional shape and the slot 630 can have a similar shape, but be sized slightly larger in order to receive the flexible strand 616 therein (e.g., a portion of the distal region 616a that includes the bond pad 618).

A cross-sectional shape of the opening 626b taken at the end 624b corresponds to a cross-sectional shape of the bulk conductor 606. For example, the bulk conductor 606 can be coiled to have a circular cross-sectional shape and the opening 626b can have similar shape, but can be sized slightly larger in order to receive a distal coiled portion of the bulk conductor 606.

In some examples, the distal coiled portion of the bulk conductor 606 is slid over a mandrel 632 (e.g., a cylindrical tube). The mandrel 632 along with the bulk conductor 606 can be installed in the opening 626b as part of connecting the bulk conductor 606 and the bond pad 618. The mandrel 632 can be formed from a conductive or a non-conductive material. For example, when the mandrel 632 and the slug 628 are formed from conductive materials, an electrical connection can be formed between contact between opposing faces of the mandrel 632 and the slug 628 within a cavity of the hybrid connector 608.

An electrical and mechanical connection is formed between the bulk conductor 606 and the bond pad 618 via the hybrid connector 608. This can be achieved by bonding the bulk conductor 606 and the bond pad 618 to the hybrid connector 608 using any suitable technique or combination of techniques. Such bonding can be achieved using a crimping technique, a thermocompression bonding technique, a thermosonic bonding technique, a resistance welding technique, a laser welding technique, conductive epoxy, and/or any other bonding technique suitable for bonding the bulk conductor 606 and/or the bond pad 618 to the hybrid connector 608.

For example, the hybrid connector 608 can be mechanically crimped to the bulk conductor 606 and the bond pad 618. In some examples, a first crimping tool can be used to crimp the body portion 622 that includes the opening 626a and a second crimping tool can be used to crimp the body portion 622 that includes the opening 626b. In some examples, a single crimping tool is used to crimp both portions of the body 622. The crimping process may also include the addition of elevated temperature and/or welding in order to mechanically and/or electrically couple the hybrid connector 608 to the bulk conductor 606 and the bond pad 618. As part of the same process or a different process, the openings 626a, 626b can be filled with a conductive epoxy to electrically connect, or further electrically connect, the bulk conductor 606 and the bond pad 618 to the hybrid connector 608.

FIGS. 8 and 9 respectively illustrate an exploded view of an example connection system 800 including a hybrid connector 808 and a profile view of the connection system 800, according to at least one example. In addition to the hybrid connector 808, the connection system 800 includes a bulk conductor 806 and a flexible strand 816.

The bulk conductor 806 can take any suitable form factor such as those described herein. For example, the bulk conductor 806 has a coiled form factor. In some examples, the coiled form may provide extensibility in the connection system 800. The flexible strand 816 can take any suitable form factor such as those described herein. For example, the flexible strand 816 can be planar and elongate. In some examples, a bond pad 818 is formed in a distal region 816a of the flexible strand 816. In this example, the bond pad 818 extends along a middle top surface of the flexible strand 816. Any of the bond pads described herein can be disposed on one or more surfaces of the flexible strands. For example, a bond pad can extend along a top surface, a bottom surface, side surfaces, and/or an end surface of an example flexible strand.

The hybrid connector 808 is formed as a sleeve defined by a body portion 822 and two ends 824a, 824b. The body portion 822 includes an opening 826a adjacent to the end 824a and an opening 826b adjacent to the end 824b. In some examples, the openings 826a, 826b are connected to each to each to define a continuous cavity within the body portion 822.

A cross-sectional shape of the opening 826a taken at the end 824a corresponds to a cross-sectional shape of the flexible strand 816. In this example, the flexible strand 816 can have a rectangular cross-sectional shape and the opening 826a can have a similar shape, but be sized slightly larger in order to receive the flexible strand 816 therein (e.g., a portion of the distal region 816a that includes the bond pad 818).

A cross-sectional shape of the opening 826b taken at the end 824b corresponds to a cross-sectional shape of the bulk conductor 806. For example, the bulk conductor 806 can be coiled to have a circular cross-sectional shape and the opening 826b can have similar shape, but can be sized slightly larger in order to receive a distal coiled portion of the bulk conductor 806.

In some examples, the distal coiled portion of the bulk conductor 806 is slid over a mandrel 832 (e.g., a cylindrical tube). The mandrel 832 along with the bulk conductor 806 can be installed in the opening 826b as part of connecting the bulk conductor 806 and the bond pad 818. The mandrel 832 can be formed from a conductive or a non-conductive material.

An electrical and mechanical connection is formed between the bulk conductor 806 and the bond pad 818 via the hybrid connector 808. This can be achieved by bonding the bulk conductor 806 and the bond pad 818 to the hybrid connector 808 using any suitable technique or combination of techniques. Such bonding can be achieved using a crimping technique, a thermocompression bonding technique, a thermosonic bonding technique, a resistance welding technique, a laser welding technique, conductive epoxy, and/or any other bonding technique suitable for bonding the bulk conductor 806 and/or the bond pad 818 to the hybrid connector 808.

For example, the hybrid connector 808 can be mechanically crimped to the bulk conductor 806 and the bond pad 818. In some examples, a first crimping tool can be used to crimp the body portion 822 that includes the opening 826a and a second crimping tool can be used to crimp the body portion 822 that includes the opening 826b. In some examples, a single crimping tool is used to crimp both portions of the body 822. The crimping process may also include the addition of elevated temperature and/or welding in order to mechanically and/or electrically couple the hybrid connector 808 to the bulk conductor 806 and the bond pad 818. As part of the same process or a different process, the openings 826a, 826b can be filled with a conductive epoxy to electrically connect, or further electrically connect, the bulk conductor 806 and the bond pad 818 to the hybrid connector 808.

Figure 10:
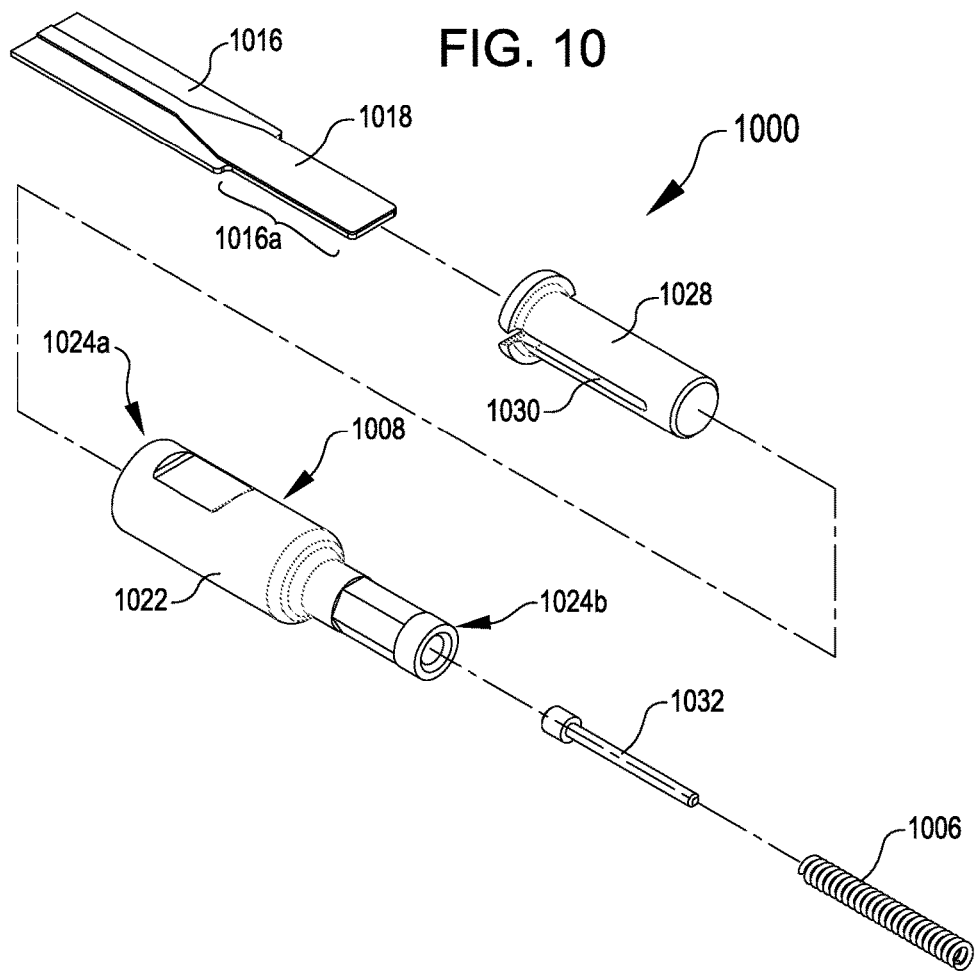
FIG. 10 illustrates an exploded view of an example connection system including a hybrid connector, according to at least one example.
Figure 11:
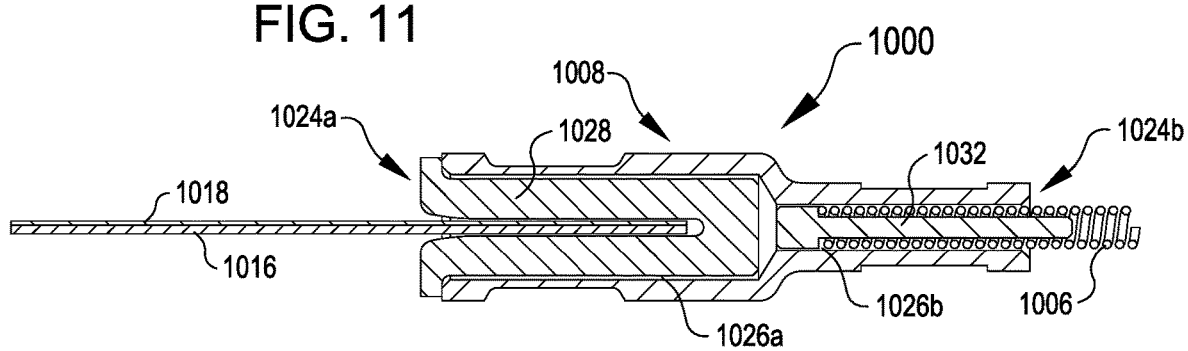
FIG. 11 illustrates a profile view of the connection system of FIG. 10, according to at least one example.

FIGS. 10 and 11 respectively illustrate an exploded view of an example connection system 1000 including a hybrid connector 1008 and a profile view of the connection system 1000, according to at least one example. In addition to the hybrid connector 1008, the connection system 1000 includes a bulk conductor 1006 and a flexible strand 1016.

The bulk conductor 1006 can take any suitable form factor such as those described herein. For example, the bulk conductor 1006 has a coiled form factor. In some examples, the coiled form may provide extensibility in the connection system 1000. The flexible strand 1016 can take any suitable form factor such as those described herein. For example, the flexible strand 1016 can be planar and elongate. In some examples, a bond pad 1018 is formed in a distal region 1016a of the flexible strand 1016. In this example, the bond pad 1018 extends along a middle top surface of the flexible strand 1016. Any of the bond pads described herein can be disposed on one or more surfaces of the flexible strands. For example, a bond pad can extend along a top surface, a bottom surface, side surfaces, and/or an end surface of an example flexible strand.

The hybrid connector 1008 is formed as a sleeve defined by a body portion 1022 and two ends 1024*a*, 1024*b*. The body portion 1022 includes an opening 1026*a* adjacent to the end 1024*a* and an opening 1026*b* adjacent to the end 1024*b*. In some examples, the openings 1026*a*, 1026*b* are connected to each to each to define a continuous cavity within the body portion 1022.

A cross-sectional shape of the opening 1026*a* taken at the end 1024*a* corresponds to a cross-sectional shape of a slug 1028 to be inserted into the opening 1026*a*. For example, the slug 1028 and the opening 1026*a* can have circular cross-sectional shapes. In some examples, the cross-sectional shapes are non-circular and uniform (e.g., square, rectangular, triangular, oval, etc.).

In some examples, the slug 1028 is formed from an electrically conductive material and is used to equally distribute crimping forces on the bond pad 1018.

The slug 1028 also includes a slot 1030. The slot 1030 is sized to receive the flexible strand 1016. In particular, the distal region 1016*a* of the flexible strand 1016 can be inserted into the slot 1030 and the slug 1028 can be inserted into the opening 1026*a*. Thus, the slot 1030 can have a cross-sectional shape that corresponds to the cross-sectional shape of the flexible strand 1016. In this example, the flexible strand 1016 can have a rectangular cross-sectional shape and the slot 1030 can have a similar shape, but be sized slightly larger in order to receive the flexible strand 1016 therein (e.g., a portion of the distal region 1016*a* that includes the bond pad 1018).

A cross-sectional shape of the opening 1026*b* taken at the end 1024*b* corresponds to a cross-sectional shape of the bulk conductor 1006. For example, the bulk conductor 1006 can be coiled to have a circular cross-sectional shape and the opening 1026*b* can have similar shape, but can be sized slightly larger in order to receive a distal coiled portion of the bulk conductor 1006. In some examples, the diameters (or other cross-sectional measurement) of the openings 1026*a*, 1026*b* are differential (e.g., the hybrid connector 1008) or uniform (e.g., the hybrid connector 608).

In some examples, the distal coiled portion of the bulk conductor 1006 is slid over a mandrel 1032 (e.g., a cylindrical tube). The mandrel 1032 along with the bulk conductor 1006 can be installed in the opening 1026*b* as part of connecting the bulk conductor 1006 and the bond pad 1018. The mandrel 1032 can be formed from a conductive or a non-conductive material. For example, when the mandrel 1032 and the slug 1028 are formed from conductive materials, an electrical connection can be formed between contact between opposing faces of the mandrel 1032 and the slug 1028 within a cavity of the hybrid connector 1008.

An electrical and mechanical connection is formed between the bulk conductor 1006 and the bond pad 1018 via the hybrid connector 1008. This can be achieved by bonding the bulk conductor 1006 and the bond pad 1018 to the hybrid connector 1008 using any suitable technique or combination of techniques. Such bonding can be achieved using a crimping technique, a thermocompression bonding technique, a thermosonic bonding technique, a resistance welding technique, a laser welding technique, conductive epoxy, and/or any other bonding technique suitable for bonding the bulk conductor 1006 and/or the bond pad 1018 to the hybrid connector 1008.

For example, the hybrid connector 1008 can be mechanically crimped to the bulk conductor 1006 and the bond pad 1018. In some examples, a first crimping tool can be used to crimp the body portion 1022 that includes the opening 1026*a* and a second crimping tool can be used to crimp the body portion 1022 that includes the opening 1026*b*. In some examples, a single crimping tool is used to crimp both portions of the body 1022. The crimping process may also include the addition of elevated temperature and/or welding in order to mechanically and/or electrically couple the hybrid connector 1008 to the bulk conductor 1006 and the bond pad 1018. As part of the same process or a different process, the openings 1026*a*, 1026*b* can be filled with a conductive epoxy to electrically connect, or further electrically connect, the bulk conductor 1006 and the bond pad 1018 to the hybrid connector 1008.

Figure 12:
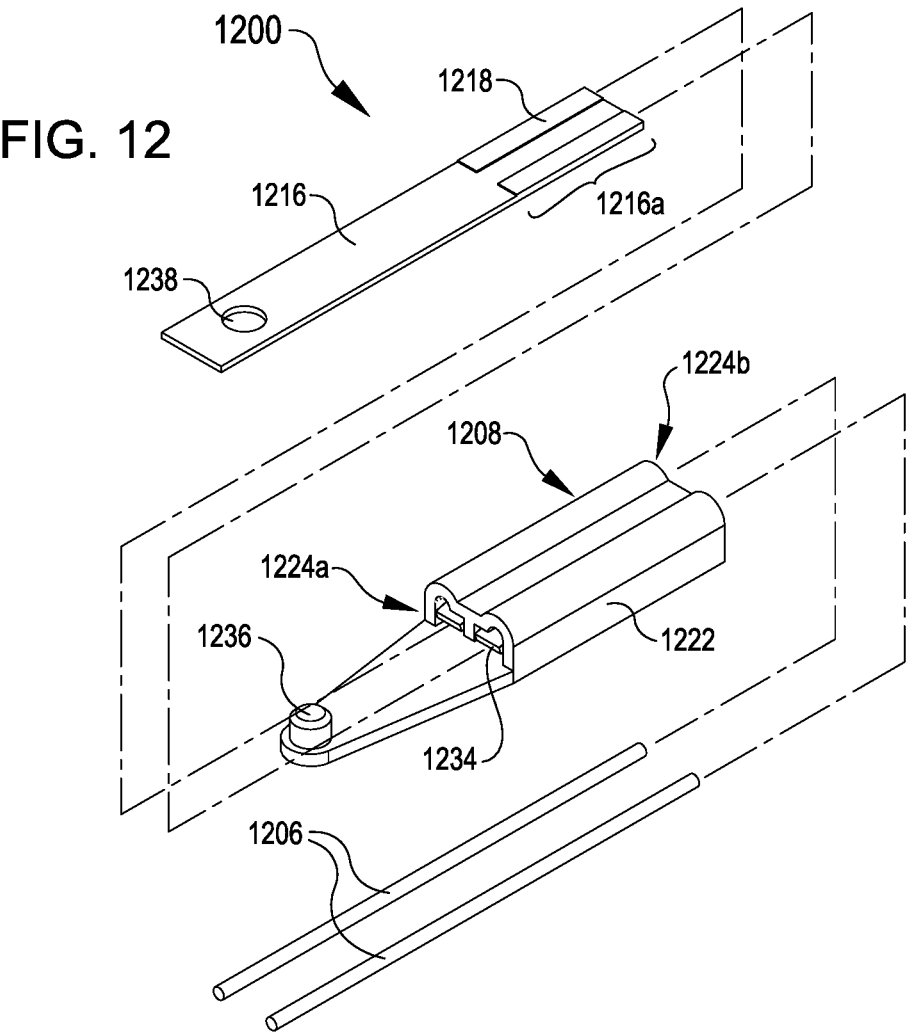
FIG. 12 illustrates an exploded view of an example connection system including a hybrid connector, according to at least one example.
Figure 13:
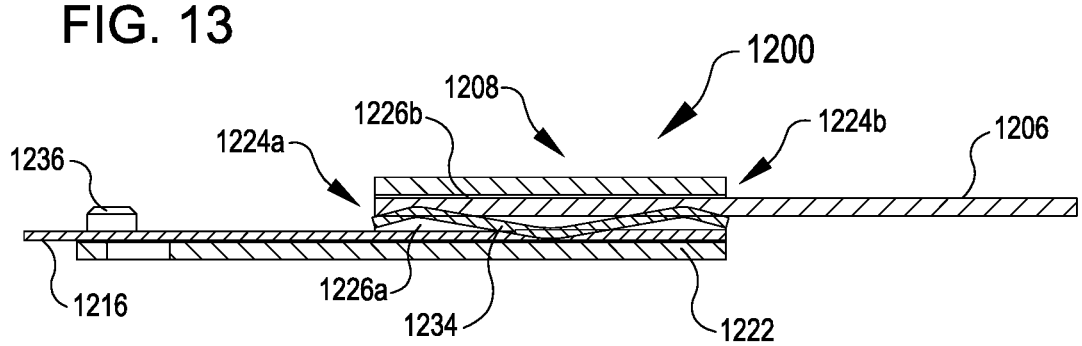
FIG. 13 illustrates a profile view of the connection system of FIG. 12, according to at least one example.

FIGS. 12 and 13 respectively illustrate an exploded view of an example connection system 1200 including a hybrid connector 1208 and a profile view of the connection system 1200, according to at least one example. In addition to the hybrid connector 1208, the connection system 1200 includes a bulk conductor 1206 and a flexible strand 1216.

The bulk conductor 1206 can take any suitable form factor such as those described herein. For example, the bulk conductor 1206 has an elongate cylindrical form factor. The flexible strand 1216 can take any suitable form factor such as those described herein. For example, the flexible strand 1216 can be planar and elongate. In some examples, a bond pad 1218 is formed in a distal region 1216*a* of the flexible strand 1216. In some examples, more than one bond pad 1218 is formed in the distal region 1216*a* of the flexible strand 1216. This second bond pad 1218 can correspond to an independent electrode or may be part of the same electrode. Any of the bond pads described herein can be disposed on one or more surfaces of the flexible strands. For example, a bond pad can extend along a top surface, a bottom surface, side surfaces, and/or an end surface of an example flexible strand.

The hybrid connector 1208 is formed as a sleeve defined by a body portion 1222 and two ends 1224*a*, 1224*b*. The body portion 1222 includes an opening 1226*a* adjacent to the end 1224*a* and an opening 1226*b* adjacent to the end 1224*b*. In some examples, the openings 1226*a*, 1226*b* are connected to each to each to define a continuous cavity within the body portion 1222. In some examples, each end 1224*a*, 1224*b* includes more than one opening 1226, which may be configured to receive respective flexible strands 1216 and bulk conductors 1206.

A cross-sectional shape of the opening 1226*a* taken at the end 1224*a* corresponds to a cross-sectional shape of the flexible strand 1216. In this example, the flexible strand 1216 can have a rectangular cross-sectional shape and the opening 1226*a* can have a similar shape, but be sized slightly larger in order to receive the flexible strand 1216 therein (e.g., a portion of the distal region 1216*a* that includes the bond pad 1218).

A cross-sectional shape of the opening 1226*b* taken at the end 1224*b* corresponds to a cross-sectional shape of the bulk conductor 1206. For example, the bulk conductor 1206 can be coiled to have a circular cross-sectional shape and the opening 1226*b* can have similar shape, but can be sized slightly larger in order to receive the bulk conductor 1206.

The hybrid connector 1208 also includes a biased member 1234. The biased member 1234 is disposed within an interior cavity of the hybrid connector 1208. The biased member 1234 can be formed from an electrically conductive material. In some examples, the biased member 1234 functions to electrically connect the bulk conductor 1206 and the bond pad 1218. This may be achieved as the biased member 1234 exerts compression forces on a distal end of the bulk conductor 1206 and on the bond pad 1218.

In some examples, the hybrid connector 1208 also includes an alignment tab 1236. The alignment tab 1236 may be used to align the flexible strand 1216 with the hybrid connector 1208. For example, the flexible strand 1216 may include an opening 1238 that corresponds in size and shape to the alignment tab 1236. In some examples, the alignment tab 1236 can be moved into place (e.g., within the opening 1238) after the flexible strand 1216 has been installed in the hybrid connector 1208.

An electrical and mechanical connection is formed between the bulk conductor 1206 and the bond pad 1218 via the biased member 1234. In some examples, the openings 1226a, 1226b can be filled with a conductive epoxy to electrically connect, or further electrically connect, the bulk conductor 1206 and the bond pad 1218 to the hybrid connector 1208.

Figure 14:
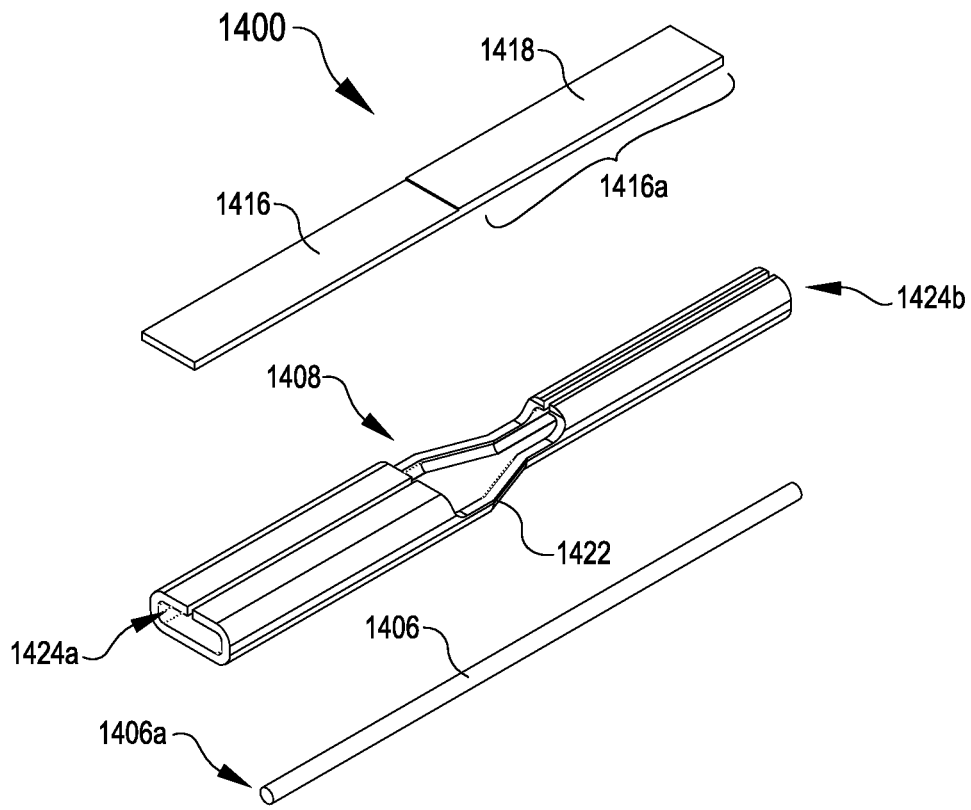
FIG. 14 illustrates an exploded view of an example connection system including a hybrid connector, according to at least one example.
Figure 15:
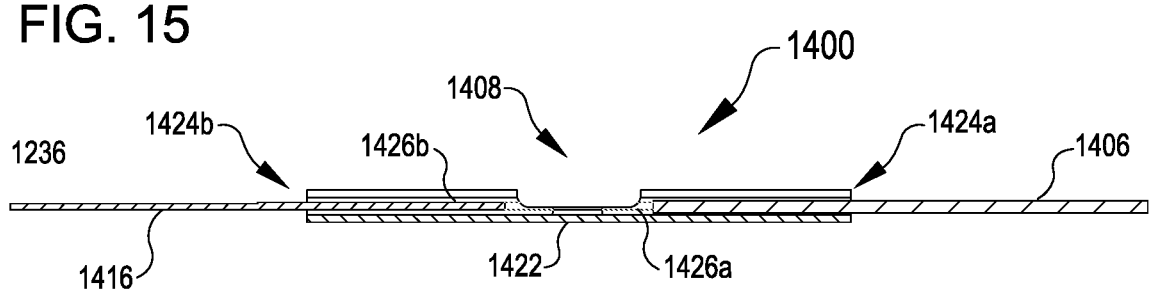
FIG. 15 illustrates a profile view of the connection system of FIG. 14, according to at least one example.

FIGS. 14 and 15 respectively illustrate an exploded view of an example connection system 1400 including a hybrid connector 1408 and a profile view of the connection system 1400, according to at least one example. In addition to the hybrid connector 1408, the connection system 1400 includes a bulk conductor 1406 and a flexible strand 1416.

The bulk conductor 1406 can take any suitable form factor such as those described herein. Likewise the flexible strand 1416 can take any suitable form factor such as those described herein. In some examples, a bond pad 1418 is formed in a distal region 1416a of the flexible strand 1416.

The hybrid connector 1408 is formed as a sleeve defined by a body portion 1422 and two ends 1424a, 1424b. The body portion 1422 includes an opening 1426a adjacent to the end 1424a and an opening 1426b adjacent to the end 1424b. In some examples, the openings 1426a, 1426b are connected to each to each to define a continuous cavity within the body portion 1422.

A cross-sectional shape of the opening 1426a taken at the end 1424a corresponds to a cross-sectional shape the flexible strand 1416. In this example, the flexible strand 1416 can have a rectangular cross-sectional shape and the opening 1426a can have a similar shape, but be sized slightly larger in order to receive the flexible strand 1416 therein (e.g., a portion of the distal region 1416a that includes the bond pad 1418).

A cross-sectional shape of the opening 1426b taken at the end 1424b corresponds to a cross-sectional shape of the bulk conductor 1406. For example, the bulk conductor 1406 can have a circular cross-sectional shape and the opening 1426b can have similar shape, but can be sized slightly larger in order to receive a distal portion of the bulk conductor 1406.

An electrical and mechanical connection is formed between the bulk conductor 1406 and the bond pad 1418 via the hybrid connector 1408. This can be achieved by bonding the bulk conductor 1406 and the bond pad 1418 to the hybrid connector 1408 using any suitable technique or combination of techniques. Such bonding can be achieved using a crimping technique, a thermocompression bonding technique, a thermosonic bonding technique, a resistance welding technique, a laser welding technique, conductive epoxy, and/or any other bonding technique suitable for bonding the bulk conductor 1406 and/or the bond pad 1418 to the hybrid connector 1408.

For example, the hybrid connector 1408 can be mechanically crimped to the bulk conductor 1406 and the bond pad 1418. In some examples, a first crimping tool can be used to crimp the body portion 1422 that includes the opening 1426a and a second crimping tool can be used to crimp the body portion 1422 that includes the opening 1426b. In some examples, a single crimping tool is used to crimp both portions of the body 1422. The crimping process may also include the addition of elevated temperature and/or welding in order to mechanically and/or electrically couple the hybrid connector 1408 to the bulk conductor 1406 and the bond pad 1418. As part of the same process or a different process, the openings 1426a, 1426b can be filled with a conductive epoxy to electrically connect, or further electrically connect, the bulk conductor 1406 and the bond pad 1418 to the hybrid connector 1408.

Figure 16:
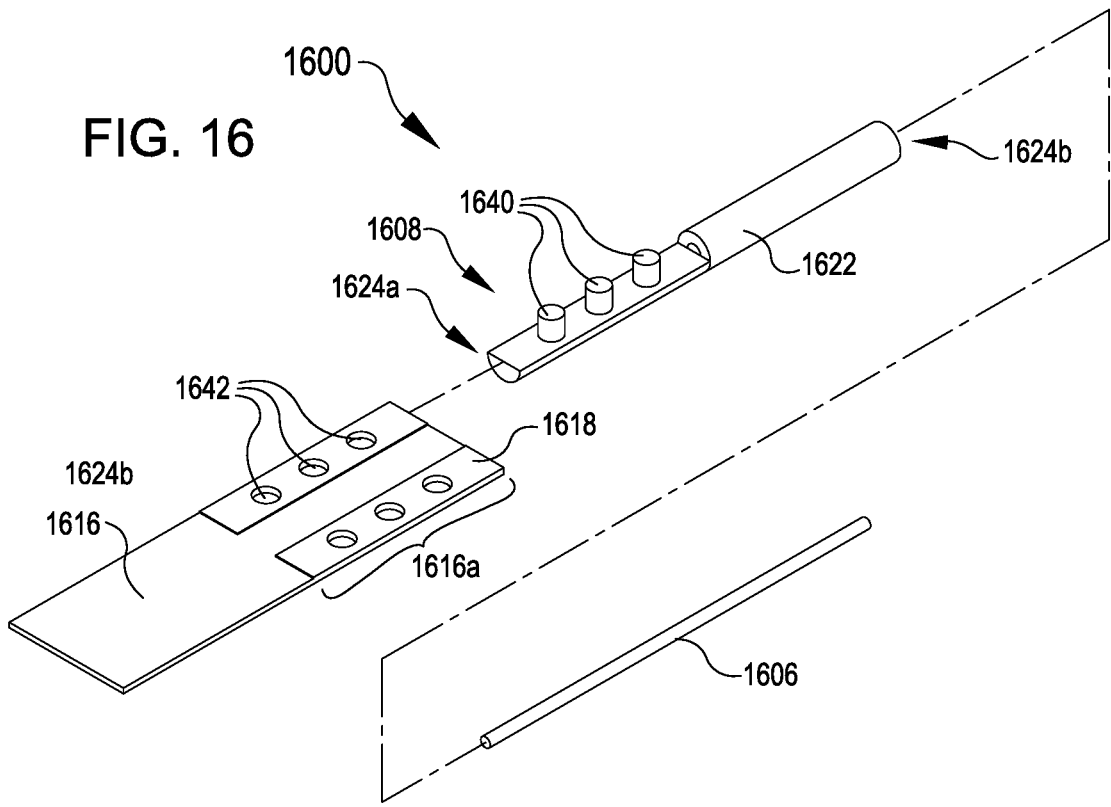
FIG. 16 illustrates an exploded view of an example connection system including a hybrid connector, according to at least one example.
Figure 17:
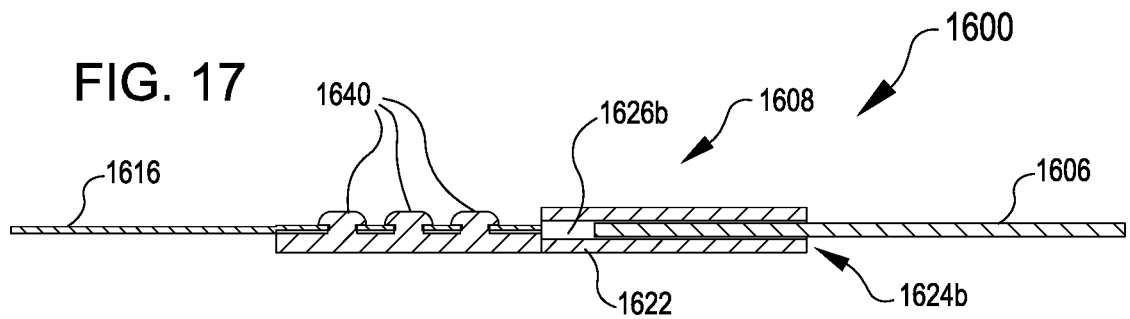
FIG. 17 illustrates a profile view of the connection system of FIG. 16, according to at least one example.

FIGS. 16 and 17 respectively illustrate an exploded view of an example connection system 1600 including a hybrid connector 1608 and a profile view of the connection system 1600, according to at least one example. In addition to the hybrid connector 1608, the connection system 1600 includes a bulk conductor 1606 and a flexible strand 1616.

The bulk conductor 1606 can take any suitable form factor such as those described herein. Likewise the flexible strand 1616 can take any suitable form factor such as those described herein. In some examples, a bond pad 1618 (or more than one bond pad 1618) is formed in a distal region 1616a of the flexible strand 1616.

The hybrid connector 1608 is formed as a sleeve defined by a body portion 1622 and two ends 1624a, 1624b. The body portion 1622 includes a set of alignment tabs 1640 adjacent to the end 1624a and an opening 1626b adjacent to the end 1624b. In some examples, the opening 1626b extends through the body portion 1622 to define a continuous cavity within the body portion 1622.

A cross-sectional shape of the opening 1626b taken at the end 1624b corresponds to a cross-sectional shape of the bulk conductor 1606. For example, the bulk conductor 1606 can have a circular cross-sectional shape and the opening 1626b can have similar shape, but can be sized slightly larger in order to receive a distal portion of the bulk conductor 1606.

The alignment tabs 1640 can correspond in shape and size to a set of alignment openings 1642 disposed within the bond pad 1618. The alignment tabs 1640 not only align the flexible strand 1616, but, once deformed, function to mechanically and electrically connect the bond pad 1618 to the hybrid connector 1208.

For example, once the alignment openings 1642 are aligned with the alignment tabs 1640 (e.g., when the alignment tabs 1640 extend through the alignment openings 1642), the alignment tabs 1640 can be deformed (e.g., like a rivet) to spread within the alignment openings 1642 and on to a top surface of the bond pad 1618. As part of the same or a different process, the other end of the hybrid connector 1608 can be mechanically crimped with the bulk conductor 1606 within the opening 1226b. In some examples, a first tool can be used to deform the alignment tabs 1640 and a second tool can be used to crimp the body portion 1622 that includes the opening 1626b. In some examples, a single tool is used to deform the alignment tabs 1640 and crimp the body portion 1622 that includes the opening 1626b. The crimping process may also include the addition of elevated temperature and/or welding in order to mechanically and/or electrically couple the hybrid connector 1608 to the bulk conductor 1606 and the bond pad 1618. As part of the same process or a different process, the opening 1626b can be filled with a conductive epoxy to electrically connect, or further electrically connect, the bulk conductor 1606 and the bond pad 1618 to the hybrid connector 1608.

In some examples, the bonding between the hybrid connector 1608 and the bond pads 1618 and the bulk conductor 1606 is achieved by bonding the bulk conductor 1606 and the bond pad 1618 to the hybrid connector 1608 using any suitable technique or combination of techniques. Such bonding can be achieved using a crimping technique, a thermocompression bonding technique, a thermosonic bonding technique, a resistance welding technique, a laser welding technique, conductive epoxy, and/or any other bonding technique suitable for bonding the bulk conductor 1606 and/or the bond pad 1618 to the hybrid connector 1608.

Figure 18:
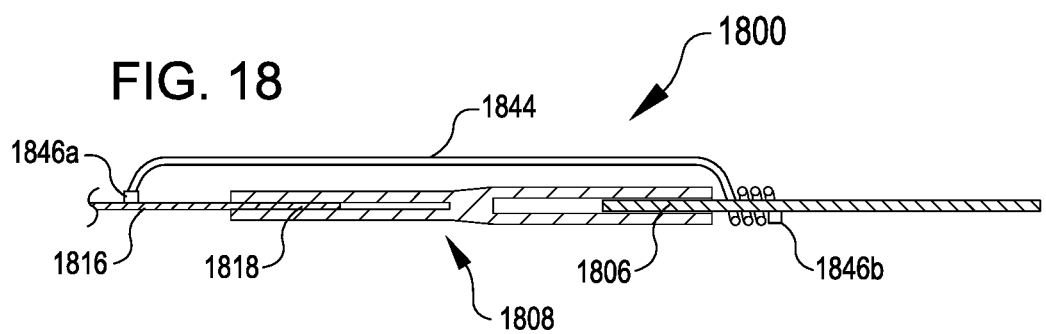
FIG. 18 illustrates a side view of an example connection system including a hybrid connector and a tension member, according to at least one example.

FIG. 18 illustrates a side view of an example connection system 1800 including a hybrid connector 1808 and a tension member 1844, according to at least one example. The connection system 1800 also includes a bulk conductor 1806 and a flexible strand 1816. The hybrid connector 1808 can be used to electrically and mechanically connect the bulk conductor 1806 and the flexible strand 1816, as described herein. The bulk conductor 1806 can take any suitable form factor such as those described herein. For example, the bulk conductor 1806 can include a coiled portion and a distal portion that extends away from the coiled portion. Likewise the flexible strand 1816 can take any suitable form factor such as those described herein. In some examples, a bond pad 1818 (or more than one bond pad 1818) is formed in a distal region of the flexible strand 1816.

The tension member 1844 can be formed from a nylon cord or other similar material. The tension member 1844 is attached to the flexible strand 1816 at attachment location 1846a and attached to the bulk conductor 1806 at attachment location 1846b. The length of the tension member 1844 (and the attachment locations 1846) is selected to be less than the length of the hybrid connector 1808. In this manner, when opposing tension forces are applied to the portion of the connection system 1800 that includes the hybrid connector 1808, the tension member 1844 will oppose the tension forces instead of the hybrid connector 1808. In this manner, the tension member 1844 functions as a limiting member to limit the extent to which the portion of the system including the hybrid connector 1808 can extend. This improves the tension cycles that the connection system 1800 can withstand. This may also prevent the connections from failing because it provides strain relief.

In some examples, strain relief may be provided by molding a tapered elastomeric material from stiff regions to the flexible regions. In this manner, the tapered elastomeric material may provide strain relief at areas where stiff regions connect to flexible regions at the hybrid connectors.

FIG. 19 illustrates a perspective view of an example flexible strand 1900 of a flexible circuit that includes a series of curves 1948, according to at least one example. The flexible strand 1900 can include a bond pad 1918. The series of curves 1948 can be located within an intermediate region 1950 of the flexible strand 1900. The intermediate region 1950 is adjacent to the bond pad 1918. In some examples, the curves 1948 are uniform and/or non-uniform. The curves 1948 may be aligned with one or more directions. For example, although illustrated as a wave oscillating with respect to a planar surface of the flexible strand 1916, the curves 1948 can also correspond to waves oscillating in other directions. The curves 1948 may add extensibility for the flexible strand 1900 and connection systems that include the flexible strand 1900. In some examples, the curves 1948 have a serpentine shape that curves onto and off of itself.

FIG. 20 illustrates an example flow diagram illustrating a process 2000 of forming a connection system, according to at least one example.

The process 2000 begins at 2002 by placing a conductive planar region of a planar strand of a flexible circuit into a first opening of a connector.

At 2004, the process 2000 includes placing an end of a bulk conductor into a second opening of the connector.

At 2006, the process 2000 includes deforming the connector to form an electrical connection between the conductive planar region and the bulk conductor. In some examples, deforming the connector includes performing a first deformation technique on a first portion of the connector adjacent to the first opening to form a first electrical connection between the conductive planar region and the connector. Deforming the connector may also include performing a second deformation technique on a second portion of the connector adjacent to the second opening to form a second electrical connection between the bulk conductor and the connector. In some examples, the first deformation technique, the second deformation technique, or both the first and second deformation techniques may include at least one of mechanical crimping, mechanical crimping in connection with elevated temperature, or mechanical crimping in connection with ultrasonic energy.

The process 2000 may also include electrically isolating the first electrical connection and the second electrical connection by applying a non-conductive epoxy or adhesive around the first and second electrical connections, molding an elastomeric, non-conductive material around the first and second electrical connections, adding a thermoplastic sleeve to the connector and reflowing under vacuum to form seals at the first and second electrical connections, performing a vacuum conformal deposition at the first and second electrical connections, and/or performing any other suitable process.

FIG. 21 illustrates an example flow diagram illustrating a process 2100 of forming a connection system, according to at least one example.

The process 2100 begins at 2102 aligning a set of openings formed in a conductive planar region of a planar strand of a flexible circuit with a set of tabs of a connector. The set of tabs is disposed at a first end of the connector.

At 2104, the process 2100 includes placing an end of a bulk conductor into an opening of the connector. The opening is disposed at a second end of the connector.

At 2106, the process 2100 includes deforming the connector to form an electrical connection between the conductive planar region and the bulk conductor. In some examples, deforming connector includes performing a first deformation technique on the set of tabs to form a first electrical connection between the conductive planar region and the connector. Deforming the connector may also include performing a second deformation technique on a portion of the connector adjacent to the opening to form a second electrical connection between the bulk conductor and the connector. In some examples, the first deformation technique, the second deformation technique, or both the first and second deformation techniques may include at least one of mechanical crimping, mechanical crimping in connection with elevated temperature, or mechanical crimping in connection with ultrasonic energy.

The process 2100 may also include electrically isolating the first electrical connection and the second electrical connection by applying a non-conductive epoxy or adhesive around the first and second electrical connections, molding an elastomeric, non-conductive material around the first and second electrical connections, adding a thermoplastic sleeve to the connector and reflowing under vacuum to form seals at the first and second electrical connections, performing a vacuum conformal deposition at the first and second electrical connections, and/or performing any other suitable process.

In the following, further examples are described to facilitate the understanding of the present disclosure.

Example 1

In this example, there is provided a system, including:
a connector defining a cavity, with a first opening formed at a first end of the connector and a second opening formed at a second end of the connector, the first opening defining a first connector cross-sectional shape; and
a flexible circuit defining a neural interface and including an elongate planar strand, the elongate planar strand including a conductive region disposed at a distal end of the elongate planar strand on a top surface of the elongate planar strand or a bottom surface of the elongate planar strand, the distal end including a strand cross-sectional shape, wherein at least a portion of the conductive region of the elongate planar strand is disposed within the first opening and permanently bonded to the connector.

Example 2

In this example, there is provided a system of any of the preceding or subsequent examples, further including a bulk conductor including a second distal end including a conductor cross-sectional shape, and wherein the second distal end of the bulk conductor is disposed within the second opening.

Example 3

In this example, there is provided a system of any of the preceding or subsequent examples, wherein the connector is permanently deformable to retain the portion of the conductive region of the elongate planar strand within the first opening and to retain the second distal end of the bulk conductor within the second opening.

Example 4

In this example, there is provided a system of any of the preceding or subsequent examples, wherein the portion of the conductive region is in physical contact with the second distal end of the bulk conductor.

Example 5

In this example, there is provided a system of any of the preceding or subsequent examples, wherein the strand cross-sectional shape corresponds to the first connector cross-sectional shape and is rectangular, and the conductor cross-sectional shape is circular.

Example 6

In this example, there is provided a system of any of the preceding or subsequent examples, further including a biased member disposed within the cavity of the connector, the biased member configured to electrically connect the bulk conductor and the conductive region.

Example 7

In this example, there is provided a system of any of the preceding or subsequent examples, wherein the bulk conductor and the elongate planar strand are disposed in different horizontal planes.

Example 8

In this example, there is provided a system of any of the preceding or subsequent examples, further including a tension member attached to the elongate planar strand and the bulk conductor, the tension member configured to support a tension force between the elongate planar strand and the bulk conductor.

Example 9

In this example, there is provided a system of any of the preceding or subsequent examples, wherein:
the system further includes a second connector; and
the flexible circuit includes a second elongate planar strand including a second conductive region, with at least a second portion of the second conductive region being disposed within a second cavity of the second connector.

Example 10

In this example, there is provided a system of any of the preceding or subsequent examples, wherein:
the elongate planar strand includes a second conductive region;
the connector defines a second cavity, with a third opening disposed at the first end of the connector and a fourth opening disposed at the second end of the connector; and
wherein at least a second portion of the second conductive region of the elongate planar strand is disposed within the second cavity via the third opening.

Example 11

In this example, there is provided a system of any of the preceding or subsequent examples, wherein:
the connector defines a second cavity, with a third opening defined at the first end of the connector and a fourth opening defined at the second end of the connector; and
the flexible circuit includes a second elongate planar strand including a second conductive region, with at least a second portion of the second conductive region being disposed within the second cavity of the connector.

Example 12

In this example, there is provided a system of any of the preceding or subsequent examples, further including a slug disposed within the cavity adjacent to the first opening, the slug defining a slot sized and oriented to receive the portion of the conductive region of the elongate planar strand.

Example 13

In this example, there is provided a system of any of the preceding or subsequent examples, wherein the strand cross-sectional shape is rectangular and corresponds to the slot and the first connector cross-sectional shape is circular and corresponds to a perimeter of the slug.

Example 14

In this example, there is provided a system of any of the preceding or subsequent examples, further including a bulk conductor coiled around a mandrel, and wherein a portion of the bulk conductor is disposed within the second opening.

Example 15

In this example, there is provided a system of any of the preceding or subsequent examples, wherein the elongate planar strand is formed to include a series of repeating curves.

Example 16

In this example, there is provided a system of any of the preceding or subsequent examples, wherein the connector is deformable to retain the portion of the conductive region of the elongate planar strand within the first opening.

Example 17

In this example, there is provided a hybrid connector, including:
a connector body;
a first connector end attached to the connector body and defining a first opening defining a first cross-sectional shape that corresponds to a first distal end of a planar flexible circuit; and
a second connector end attached to the connector body opposite the first connector end and defining a second opening defining a second cross-sectional shape that corresponds to a second distal end of a bulk conductor.

Example 18

In this example, there is provided a hybrid connector of any of the preceding or subsequent examples, wherein the first cross-sectional shape is rectangular and the second cross-sectional shape is non-rectangular.

Example 19

In this example, there is provided a hybrid connector of any of the preceding or subsequent examples, wherein the first cross-sectional shape and the second cross-sectional shape are circular.

Example 20

In this example, there is provided a hybrid connector of any of the preceding or subsequent examples, wherein the connector body defines a cavity connecting the first opening with the second opening.

Example 21

In this example, there is provided a hybrid connector of any of the preceding or subsequent examples, wherein the cavity has a uniform diameter between the first opening and the second opening.

Example 22

In this example, there is provided a hybrid connector of any of the preceding or subsequent examples, wherein:
the first cross-sectional shape is circular; and
the first opening is sized to receive a cylindrical slug including a slot that corresponds to the first distal end of the planar flexible circuit.

Example 23

In this example, there is provided a hybrid connector of any of the preceding or subsequent examples, wherein the connector body is deformable to retain the first distal end of the elongate planar strand within the first opening and to retain the second distal end of the bulk conductor within the second opening.

Example 24

In this example, there is provided a hybrid connector of any of the preceding or subsequent examples, wherein the connector body is deformable using at least one of a thermocompression bonding technique, a thermosonic bonding technique, a resistance welding technique, or a laser welding technique.

Example 25

In this example, there is provided a hybrid connector of any of the preceding or subsequent examples, further including a biased member disposed within a cavity of the connector body between the first end and the second end, the biased member configured to electrically connect the first distal end of the elongate planar strand and the second distal end of the bulk conductor.

Example 26

In this example, there is provided a hybrid connector of any of the preceding or subsequent examples, further including a set of anchors disposed adjacent to at least one of the first opening or the second opening.

Example 27

In this example, there is provided a hybrid connector, including:
a connector body;
a first connector end attached to the connector body, the first connector end including a set of raised tabs corresponding to a set of openings formed in a distal region of a planar flexible circuit; and
a second connector end attached to the connector body opposite the first connector end, the second connector end defines an opening defining a cross-sectional shape that corresponds to a distal end of a bulk conductor.

Example 28

In this example, there is provided a hybrid connector of any of the preceding or subsequent examples, wherein:
the set of raised tabs is deformable using a first deformation technique to form a first electrical connection between the connector body and the distal region of the planar flexible circuit; and
a portion of the connector body adjacent to the second connector end is deformable using a second deformation technique to form a second electrical connection between the connector body and the bulk conductor.

Example 29

In this example, there is provided a system, including:
a neural interface including an elongate planar strand, the elongate planar strand including a conductive region disposed at a first distal end of the elongate planar strand, the first distal end including a first cross-sectional shape;
a bulk conductor including a second distal end including a second cross-sectional shape; and a connector disposed between the elongate planar strand and the bulk conductor, the connector including:
  a first end in which is formed a first opening corresponding to the first cross-sectional shape, the first distal end being held within the first opening; and
  a second end in which is formed a second opening corresponding to the second cross-sectional shape, the second distal end being held within the second opening,
wherein an electrical connection is formed between the conductive region and the bulk conductor via the connector.

Example 30

In this example, there is provided a method of forming a hybrid connection, including:
  placing a conductive planar region of a planar strand of a flexible circuit into a first opening of a connector;
  placing an end of a bulk conductor into a second opening of the connector; and
  deforming the connector to form an electrical connection between the conductive planar region and the bulk conductor.

Example 31

In this example, there is provided a method of any of the preceding or subsequent examples, wherein deforming the connector includes:
  performing a first deformation technique on a first portion of the connector adjacent to the first opening to form a first electrical connection between the conductive planar region and the connector; and
  performing a second deformation technique on a second portion of the connector adjacent to the second opening to form a second electrical connection between the bulk conductor and the connector,
  wherein the first deformation technique, the second deformation technique, or both the first and second deformation techniques comprise at least one of mechanical crimping, mechanical crimping in connection with elevated temperature, or mechanical crimping in connection with ultrasonic energy.

Example 32

In this example, there is provided a method of any of the preceding or subsequent examples, further comprising electrically isolating the first electrical connection and the second electrical connection by applying a non-conductive epoxy or adhesive around the first and second electrical connections, molding an elastomeric, non-conductive material around the first and second electrical connections, adding a thermoplastic sleeve to the connector and reflowing under vacuum to form seals at the first and second electrical connections, and/or performing a vacuum conformal deposition at the first and second electrical connections.

Example 33

In this example, there is provided a method of forming a hybrid connection, including:
  aligning a set of openings formed in a conductive planar region of a planar strand of a flexible circuit with a set of tabs of a connector, the set of tabs disposed at a first end of the connector;
  placing an end of a bulk conductor into an opening of the connector, the opening disposed at a second end of the connector; and
  deforming the connector to form an electrical connection between the conductive planar region and the bulk conductor.

Example 34

In this example, there is provided a method of any of the preceding or subsequent examples, wherein deforming the connector includes:
  performing a first deformation technique on the set of tabs to form a first electrical connection between the conductive planar region and the connector; and
  performing a second deformation technique on a portion of the connector adjacent to the opening to form a second electrical connection between the bulk conductor and the connector,
  wherein the first deformation technique, the second deformation technique, or both the first and second deformation techniques comprise at least one of mechanical crimping, mechanical crimping in connection with elevated temperature, or mechanical crimping in connection with ultrasonic energy.

Example 35

In this example, there is provided a method of any of the preceding or subsequent examples, further comprising electrically isolating the first electrical connection and the second electrical connection by applying a non-conductive epoxy or adhesive around the first and second electrical connections, molding an elastomeric, non-conductive material around the first and second electrical connections, adding a thermoplastic sleeve to the connector and reflowing under vacuum to form seals at the first and second electrical connections, and/or performing a vacuum conformal deposition at the first and second electrical connections.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

What is claimed is:

1. A system, comprising:
   a connector defining a cavity, with a first opening formed at a first end of the connector and a second opening formed at a second end of the connector, the first opening defining a first connector cross-sectional shape; and
   a flexible circuit defining a neural interface and comprising an elongate planar strand, the elongate planar strand comprising a conductive region disposed at a distal end of the elongate planar strand on a top surface of the elongate planar strand or a bottom surface of the elongate planar strand, the distal end comprising a strand cross-sectional shape,
   wherein at least a portion of the conductive region of the elongate planar strand is disposed within the first opening and permanently bonded to the connector.

2. The system of claim 1, further comprising a bulk conductor comprising a second distal end comprising a conductor cross-sectional shape, and wherein the second distal end of the bulk conductor is disposed within the second opening.

3. The system of claim 2, wherein the connector is permanently deformable to retain the portion of the conductive region of the elongate planar strand within the first opening and to retain the second distal end of the bulk conductor within the second opening.

4. The system of claim 2, wherein the portion of the conductive region is in physical contact with the second distal end of the bulk conductor.

5. The system of claim 2, wherein the strand cross-sectional shape corresponds to the first connector cross-sectional shape and is rectangular, and the conductor cross-sectional shape is circular.

6. The system of claim 2, further comprising a biased member disposed within the cavity of the connector, the biased member configured to electrically connect the bulk conductor and the conductive region.

7. The system of claim 6, wherein the bulk conductor and the elongate planar strand are disposed in different horizontal planes.

8. The system of claim 2, further comprising a tension member attached to the elongate planar strand and the bulk conductor, the tension member configured to support a tension force between the elongate planar strand and the bulk conductor.

9. The system of claim 1, wherein:
   the system further comprises a second connector; and
   the flexible circuit comprises a second elongate planar strand comprising a second conductive region, with at least a second portion of the second conductive region being disposed within a second cavity of the second connector.

10. The system of claim 1, wherein:
    the elongate planar strand comprises a second conductive region;
    the connector defines a second cavity, with a third opening disposed at the first end of the connector and a fourth opening disposed at the second end of the connector; and
    wherein at least a second portion of the second conductive region of the elongate planar strand is disposed within the second cavity via the third opening.

11. The system of claim 1, wherein:
    the connector defines a second cavity, with a third opening defined at the first end of the connector and a fourth opening defined at the second end of the connector; and
    the flexible circuit comprises a second elongate planar strand comprising a second conductive region, with at least a second portion of the second conductive region being disposed within the second cavity of the connector.

12. The system of claim 1, further comprising a slug disposed within the cavity adjacent to the first opening, the slug defining a slot sized and oriented to receive the portion of the conductive region of the elongate planar strand.

13. The system of claim 12, wherein the strand cross-sectional shape is rectangular and corresponds to the slot and the first connector cross-sectional shape is circular and corresponds to a perimeter of the slug.

14. The system of claim 1, further comprising a bulk conductor coiled around a mandrel, and wherein a portion of the bulk conductor is disposed within the second opening.

15. The system of claim 1, wherein the elongate planar strand is formed to include a series of repeating curves.

16. The system of claim 1, wherein the connector is deformable to retain the portion of the conductive region of the elongate planar strand within the first opening.

17. A hybrid connector, comprising:
    a connector body;
    a first connector end attached to the connector body and defining a first opening defining a first cross-sectional shape that corresponds to a first distal end of a planar flexible circuit; and
    a second connector end attached to the connector body opposite the first connector end and defining a second opening defining a second cross-sectional shape that corresponds to a second distal end of a bulk conductor.

18. The hybrid connector of claim 17, wherein the first cross-sectional shape is rectangular and the second cross-sectional shape is non-rectangular.

19. The hybrid connector of claim 17, wherein the first cross-sectional shape and the second cross-sectional shape are circular.

20. The hybrid connector of claim 17, wherein the connector body defines a cavity connecting the first opening with the second opening.

21. The hybrid connector of claim 20, wherein the cavity has a uniform diameter between the first opening and the second opening.

22. The hybrid connector of claim 17, wherein:
    the first cross-sectional shape is circular; and
    the first opening is sized to receive a cylindrical slug comprising a slot that corresponds to the first distal end of the planar flexible circuit.

23. The hybrid connector of claim 17, wherein the connector body is deformable to retain the first distal end of the planar flexible circuit within the first opening and to retain the second distal end of the bulk conductor within the second opening.

24. The hybrid connector of claim 23, wherein the connector body is deformable using at least one of a thermocompression bonding technique, a thermosonic bonding technique, a resistance welding technique, or a laser welding technique.

25. The hybrid connector of claim 17, further comprising a biased member disposed within a cavity of the connector body between the first distal end and the second distal end, the biased member configured to electrically connect the first distal end of the planar flexible circuit and the second distal end of the bulk conductor.

26. The hybrid connector of claim 17, further comprising a set of anchors disposed adjacent to at least one of the first opening or the second opening.

27. A hybrid connector, comprising:
a connector body;
a first connector end attached to the connector body, the first connector end comprising a set of raised tabs corresponding to a set of openings formed in a distal region of a planar flexible circuit; and
a second connector end attached to the connector body opposite the first connector end, the second connector end defines an opening defining a cross-sectional shape that corresponds to a distal end of a bulk conductor.

28. The hybrid connector of claim 27, wherein:
the set of raised tabs is deformable using a first deformation technique to form a first electrical connection between the connector body and the distal region of the planar flexible circuit; and
a portion of the connector body adjacent to the second connector end is deformable using a second deformation technique to form a second electrical connection between the connector body and the bulk conductor.

29. A system, comprising:
a neural interface comprising an elongate planar strand, the elongate planar strand comprising a conductive region disposed at a first distal end of the elongate planar strand, the first distal end comprising a first cross-sectional shape;
a bulk conductor comprising a second distal end comprising a second cross-sectional shape; and
a connector disposed between the elongate planar strand and the bulk conductor, the connector comprising:
a first end in which is formed a first opening corresponding to the first cross-sectional shape, the first distal end being held within the first opening; and
a second end in which is formed a second opening corresponding to the second cross-sectional shape, the second distal end being held within the second opening,
wherein an electrical connection is formed between the conductive region and the bulk conductor via the connector.

30. A method of forming a hybrid connection, the method comprising:
placing a conductive planar region of a planar strand of a flexible circuit into a first opening of a connector;
placing an end of a bulk conductor into a second opening of the connector; and
deforming the connector to form an electrical connection between the conductive planar region and the bulk conductor.

31. The method of claim 30, wherein deforming the connector comprises:
performing a first deformation technique on a first cavity portion of the connector adjacent to the first opening to form a first electrical connection between the conductive planar region and the connector; and
performing a second deformation technique on a second cavity portion of the connector adjacent to the second opening to form a second electrical connection between the bulk conductor and the connector,
wherein the first deformation technique, the second deformation technique, or both the first and second deformation techniques comprise at least one of mechanical crimping, mechanical crimping in connection with elevated temperature, or mechanical crimping in connection with ultrasonic energy.

32. The method of claim 31, further comprising electrically isolating the first electrical connection and the second electrical connection by applying a non-conductive epoxy or adhesive around the first and second electrical connections, molding an elastomeric, non-conductive material around the first and second electrical connections, adding a thermoplastic sleeve to the connector and reflowing under vacuum to form seals at the first and second electrical connections, and/or performing a vacuum conformal deposition at the first and second electrical connections.

33. A method of forming a hybrid connection, the method comprising:
aligning a set of openings formed in a conductive planar region of a planar strand of a flexible circuit with a set of tabs of a connector, the set of tabs disposed at a first end of the connector;
placing an end of a bulk conductor into an opening of the connector, the opening disposed at a second end of the connector; and
deforming the connector to form an electrical connection between the conductive planar region and the bulk conductor.

34. The method of claim 33, wherein deforming the connector comprises:
performing a first deformation technique on the set of tabs to form a first electrical connection between the conductive planar region and the connector; and
performing a second deformation technique on a portion of the connector adjacent to the opening to form a second electrical connection between the bulk conductor and the connector,
wherein the first deformation technique, the second deformation technique, or both the first and second deformation techniques comprise at least one of mechanical crimping, mechanical crimping in connection with elevated temperature, or mechanical crimping in connection with ultrasonic energy.

35. The method of claim 34, further comprising electrically isolating the first electrical connection and the second electrical connection by applying a non-conductive epoxy or adhesive around the first and second electrical connections, molding an elastomeric, non-conductive material around the first and second electrical connections, adding a thermoplastic sleeve to the connector and reflowing under vacuum to form seals at the first and second electrical connections, and/or performing a vacuum conformal deposition at the first and second electrical connections.

* * * * *